United States Patent
Gooßen et al.

(10) Patent No.: US 8,877,958 B2
(45) Date of Patent: Nov. 4, 2014

(54) METHOD TO PREPARE BETA-FUNCTIONALIZED ALIPHATIC ESTERS

(75) Inventors: Lukas J. Gooßen, Kaiserslautern (DE); Dominik Ohlmann, Namborn-Roschberg (DE); Markus Dierker, Düsseldorf (DE)

(73) Assignee: Cognis IP Management GmbH, Duesseldorf (DE)

( * ) Notice: Subject to any disclaimer, the term of this patent is extended or adjusted under 35 U.S.C. 154(b) by 12 days.

(21) Appl. No.: 13/881,853

(22) PCT Filed: Aug. 31, 2011

(86) PCT No.: PCT/EP2011/004400
§ 371 (c)(1),
(2), (4) Date: Apr. 26, 2013

(87) PCT Pub. No.: WO2012/055455
PCT Pub. Date: May 3, 2012

(65) Prior Publication Data
US 2013/0225852 A1   Aug. 29, 2013

(30) Foreign Application Priority Data
Oct. 28, 2010   (EP) .................................. 10189314

(51) Int. Cl.
C07C 69/612   (2006.01)
C07C 229/12   (2006.01)
C07C 227/06   (2006.01)
C07D 211/34   (2006.01)
C07D 295/15   (2006.01)
C07C 227/08   (2006.01)
C07D 211/62   (2006.01)
C07D 211/76   (2006.01)
C07C 67/347   (2006.01)

(52) U.S. Cl.
CPC ............ *C07C 67/347* (2013.01); *C07D 211/34* (2013.01); *C07C 2101/14* (2013.01); *C07D 295/15* (2013.01); *C07C 227/08* (2013.01); *C07D 211/62* (2013.01); *C07C 227/06* (2013.01); *C07D 211/76* (2013.01)
USPC ........................... 560/103; 560/125; 560/155

(58) Field of Classification Search
None
See application file for complete search history.

(56) References Cited

PUBLICATIONS

Behr, Arno et al., "Isomerizing hydroformylation of fatty acid esters: Formation of m-aldehydes", *Eur. J. Lipid Sci. Technol.* vol. 107 (2005) pp. 213-219.
Ghebreyessus, Kesete Y. et al., "Isomerizing-Hydroboration of the Monounsaturated Fatty Acid Ester Methyl Oleate", *Organometallics 2006*, 25, pp. 3040-3044.
Ohlmann, D. et al., "Regioselectivesynthesis of [beta]-Amino-substituted aliphatic esters by Rhodium-catalyzed tandem double-bond Migration/conjugate addition", *Chemistry: A European Journal*, vol. 17, 2011, pp. 9508-9519.
Singer, H. et al., "Isomerisierungen Olefinishcer Carbonsäureester Mit Rhodiumkomplexen", *Tetrahedron*, vol. 28. 1972, pp. 5796-5777.
Takaya, Yoshiaki et al., "Rhodium-catalyzed asymmetric 1,4-addition of arylboron reagents to α,β-unsaturated esters", *Tetrahedron*: vol. 10 (1999) pp. 4047-4056.

*Primary Examiner* — Jafar Parsa
*Assistant Examiner* — Amy C Bonaparte
(74) *Attorney, Agent, or Firm* — Servilla Whitney LLC

(57) ABSTRACT

The invention pertains to a new route to prepare β-functionalized carboxylic acid esters in a one-pot reaction, by reacting an olefinic acid ester in the presence of a catalyst system, comprising a Rh(I)-complex, together with an aryl boron or a diamine as nucleophilic compounds, and under oxygen-free conditions and elevated temperatures.

8 Claims, No Drawings

METHOD TO PREPARE BETA-FUNCTIONALIZED ALIPHATIC ESTERS

CROSS-REFERENCE TO RELATED APPLICATIONS

This application is the national stage entry of PCT/EP2011/004400, filed on Aug. 31, 2011, which claims priority to European Patent application number 10189314.7, filed on Oct. 28, 2010, both of which are incorporated herein by reference in their entireties.

FIELD

The present invention pertains to a method for preparing β-functionalized carboxylic acid ester.

BACKGROUND

The controlled and selective migration of C—C double bonds is of high synthetic value, because it facilitates in situ access to certain isomers for functionalizations, which would not be feasible otherwise. Unsaturated aliphatic carboxylic esters, amongst them fatty esters, have been studied as substrates for these isomerization reactions since more than 60 years. The double bond migration of olefins has been combined with several functionalization reactions, like hydroboration, butenolysis, methathesis, methoxycarbonylation, hydroformylation hydroaminomethylation. Especially for long-chain unsaturated fatty esters from renewable feedstocks, isomerizing functionalizations are only known to a small extend, and these examples from the literature have in common that the trapping reaction takes place at the methyl terminus of the alkyl chain, see for example publications K. Y. Ghebreyessus, R. J. Angelici, Organometallics 2006, 25, 3040-3044.

Thus, there is a constant need for the development of new or the improvement of known reactions and reaction sequences which lead to β-functionalized aliphatic esters. Especially preferred are reaction sequences which allow obtaining the product in a one-pot reaction rather than using various different and cost generating reaction steps.

SUMMARY

It was found that a rhodium-catalyzed double bond isomerization/conjugate addition will provide a valuable new approach to prepare β-functionalized esters.

The present invention therefore pertains to a method for preparing β-functionalized carboxylic acid esters according to formula (I)

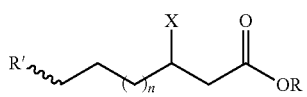
(I)

whereby R represents an alkyl group with 1 to 8 C-atoms, R' stands for a hydrogen atom, or an alkyl moiety with 1 to 8 C-atoms, and n stands for zero, or a number of 1 to 20, and X represents either a group Ph-R" whereby R" represents an hydrogen atom or an alkyl group with 1 to 6 C-atoms, or an group R"'—N—R"", whereby R"' and R"" stand independently for linear or branched or cyclic alkyls with 1 to 8 C-atoms, characterized in reacting in one-pot an unsaturated ester according to general formula (II)

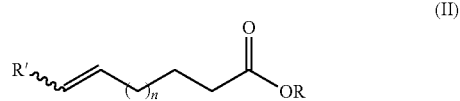
(II)

whereby n, R and R' have the same meaning as in formula (I), in the presence of either an a boron compound according to formula (III) where M represents an anion, and R" has the same meaning as for formula (I),

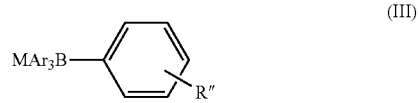
(III)

or an amine R"'—NH—R"" (IV), whereby R"' and R"" have the same meaning as above and a rhodium containing catalyst, under an oxygen-free atmosphere at temperatures between 80-120° C. in a solvent.

DETAILED DESCRIPTION

Based on the principle of the thermodynamic equilibrium of isomers, the method according to the present application is a catalytic one-pot method that allows the access of remote double bonds in olefinic esters for the reaction with nucleophiles into β-functionalized compounds. From a rapidly inter-converting pool of positional double bond isomers, only the α,β-unsaturated species is depleted by the conjugate addition reaction, and it is replenished by the other isomers with which it is in reversible equilibrium. A similar example would be the intra molecular case of the catalytic lactonization of unsaturated fatty acids developed earlier by our group. The development of this new tandem reaction was done by separate examination of the two sub-steps, as there are isomerization and conjugate addition.

The substrate is a carboxylic acid ester (II) with one C—C double bond in the alkyl part of the acid. Preferred are olefinic acid esters (II) with at least 5 C-atoms in the acid part, up to 22 C-atoms. These compounds can be prepared by know methods and are commercially available.

Especially preferred are unsaturated acids, obtained from natural sources, like oils and fats—in this regard oleic acid or elaidic acid are examples for such unsaturated acids.

The reaction according to the present invention takes place in a solvent, which is preferably selected from benzene, toluene, chlorobenzene, diphenyl ether or blends of water and the forgoing solvents. It is possible to carry out the reaction under water-free conditions too. Preferred solvents are aromatic ones, and in particular toluene. Further preferred is the use of an organic solvent blended with water, whereby blends comprising from 60 to 90% toluene and 40 to 10% water are of advantage. In a preferred embodiment the solvent is selected from toluene, or a blend of water and toluene in a weight ration of 1:25 to 1:10, and preferably of 1:20.

A further condition to carry out the method is the absence of oxygen ($O_2$) during the reaction. Therefore, it is preferred to carry out the reaction under nitrogen ($N_2$) or argon (Ar) atmosphere, but under normal pressure.

The reaction need an elevated temperature in the range from 80 to 120° C., and more preferred from 100 to 110° C. to be carried out. Reaction time is depended from the amounts used, but typically it needs between 15 to 25 h to complete the reaction.

The catalysts used are selected from Rh-containing catalysts, preferably comprising a Rh atom with an oxidation number +1. Especially proffered are complexes of Rh with various organic ligands. Here one embodiment of the present teaching pertains to rhodium containing catalysts which are particularly selected from (i) Rh(acac)(COD), [Rh(OH)(COD)]$_2$ or [Rh(Cl)(COD)]$_2$ and most preferred together with (ii) a Biphephos or P(Oallyl)$_3$ ligand in molar amounts of (i):(ii) of 2:1 to 1:2, and preferably of 1:1.

The second compound, used in the reaction is a nucelophile, selected from either a Boron compound (III), or a diamine (IV). Preferred boron compounds are selected from the group comprising PhB(OH)$_2$, PhB(pin), PhBMIDA ester, PhBF$_3$K, KB(4-ClC$_6$H$_4$)$_4$, NaB(2-naphthyl)$_4$, NaB(4-tolyl)$_4$, and KB(2-thienyl)$_4$. Such Rh-complexes are well known and commercial available, see publication of A. Behr, D. Obst, A. Westfechtel, Eur. J. Lipid Sci. Technol. 2005, 107, 213-219.

As amines in particular cyclic diamines are used, like pyrrols, pyrrolines and pyrrolidines are selected.

The reaction itself can be carried out be simply blending the compelling compounds together and subsequently heat the blend to the reaction temperature. After the reaction is terminated, and cooled, the product could be isolated by known separation means, whereby chromatographic methods are preferred.

Overviews about β-esters, which have been prepared according to the present teaching and according to the following reaction scheme, are listed in the following table I:

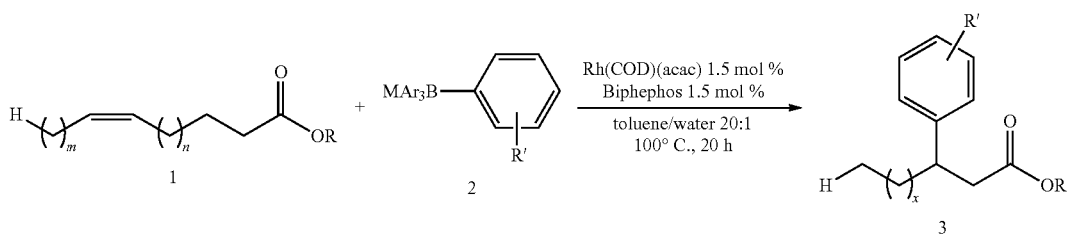

| Entry | Ester | Borate | Product | Yield (%)[b] |
|---|---|---|---|---|
| 1 | 1a | NaBPh$_4$ (2a) | 3a | 89 |
| 2 | 1c | 2a | 3c | 81 |
| 3 | 1d | 2a | 3d | 63 |
| 4 | 1e | 2a | 3e | 60 |

-continued
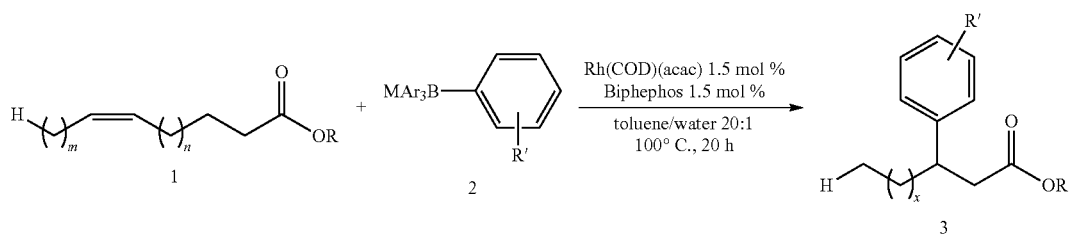
| Entry | Ester | Borate | Product | Yield (%)[b] |
|---|---|---|---|---|
| 5 | 1f | 2a | 3f | 30 |
| 6 | 1g | 2a | 3g | 62 |
| 7 | 1h | 2a | 3h | 45 |
| 8 | 1a | KB(4-ClC$_6$H$_4$)$_4$ (2b) | 3j | 56[d] |
| 9 | 1a | NaB(2-naphthyl)$_4$ (2c) | 3k | 44 |

-continued

| Entry | Ester | Borate | Product | Yield (%)[b] |
|---|---|---|---|---|
| 10 | 1a | NaB(4-tolyl)$_4$ (2d) | 3l | 92 |
| 11 | 1a | KB(2-thienyl)$_4$ (2e) | 3m | 0 |

The reaction conditions were: 0.5 mmol enoate 1, 2.0 mmol tetraarylborate 2, Rh(acac)(COD) 0.015 mmol, BIPHEPHOS 0.015 mmol, toluene/water 3.0/0.15 mL, 100° C., 20 h, argon atmosphere.
[a] N corresponds to the number of possible isomers.
[b] isolated yields.
[c] 0.03 mmol of catalyst were used.
[d] 2.0 equiv. of 18-crown-6 were added.

The following Table II displays reaction products from amines and olefinic esters according to the following reaction scheme:

| Entry | Ester | Product | Yield (%)[a] |
|---|---|---|---|
| 1 | 1c | 5a | 44 |
| 2 | 1c | 5b | 62 |

-continued
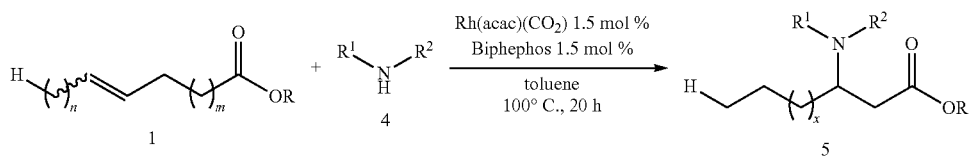
| Entry | Ester | Product | Yield (%)[a] |
|---|---|---|---|
| 3 | 1c | 5c | 89 |
| 4 | 1c | 5d | 74 |
| 5 | 1c | 5e | 71 |
| 6 | 1c | 5f | 47 |
| 7 | 1d | 5g | 25 |
| 8 | 1f | 5h | 17 |

-continued

Reaction scheme:

H–(CH=CH)ₙ–(CH₂)ₘ–C(O)–OR (1) + R¹R²NH (4) →[Rh(acac)(CO)₂ 1.5 mol%, Biphephos 1.5 mol%, toluene, 100°C, 20 h]→ R¹R²N–(CH₂)...–CH(...)–(CH₂)ₓ–C(O)–OR (5)

| Entry | Ester | Product | Yield (%)[a] |
|---|---|---|---|
| 9 | ethyl pent-4-enoate (1c) | 5i (piperidinone-substituted ethyl ester) | 35[b] |
| 10 | ethyl pent-4-enoate (1c) | 5k (PhNH-substituted ethyl ester) | 0 | reaction conditions: 0.5-1.0 mmol enoate 1, 5.0-10.0 mmol amine 4, Rh(acac)(CO)₂ 0.015 equiv., BIPHEPHOS 0.015 equiv., toluene 2.0 mL/mmol, 100° C., 20 h, argon atmosphere.

The extension of this new reaction pathway to fatty esters or triglycerides could be a helpful tool for the exploration of plant oils as renewable feedstock.

The products obtained by the method according to the invention could be used to prepare cosmetic compositions. Particularly, the use as oil phase or emollient is preferred. Furthermore, the compounds are suitable to solve various kinds of UV filters.

EXAMPLES

Preparation Examples

General Methods

Reactions were performed under a nitrogen atmosphere in oven-dried glassware containing a teflon-coated stirrer bar and dry septum. For the exclusion of atmospheric oxygen from the reaction media, solvents were degassed by 45 min argon sparging before the reagents were mixed. Solvents were purified by standard procedures prior to use. All reactions were monitored by GC using n-dodecane as an internal standard. Response factors of the products with regard to n-dodecane were obtained experimentally by analyzing known quantities of the substances. GC analyses were carried out using an HP-5 capillary column (Phenyl Methyl Siloxane 30 m×320×0.25, 100/2.3-30-300/3) and a time program beginning with 2 min at 60° C., followed by 30° C./min ramp to 300° C., then 3 min at this temp. Column chromatography was performed using a Combi Flash Companion-Chromatography-System (Isco-Systems) and RediSep packed columns (12 g). TLC analyses were performed on commercial 60 $F_{254}$ silica gel plates. NMR spectra were obtained on Bruker AMX 200, AMX 400 or on Bruker Avance 600 systems using $CDCl_3$ as solvent, with proton and carbon resonances at 200, 400 or 600 MHz and 51, 101 or 151 MHz, respectively. Mass spectral data were acquired on a GC-MS Saturn 2100 T (Varian). Commercial substrates were used as received unless otherwise stated. Non-commercial olefinic esters 1 were synthesized from the corresponding acids using standard esterification methods.

General Procedure for the Isomerization-Conjugate Addition Reaction of Arylborates An oven-dried 20 mL crimp top vial was charged with acetylacetonato(1,5-cyclooctadiene)rhodium(I) (1.5 mol %), Biphephos (1.5 mol %), arylborate salt (2.0 equiv.) and stir bar, sealed with a Teflon septum and evacuated-purged with argon three times. Subsequently, toluene (3 mL/mmol ester), olefinic ester 1 (0.5-1.0 mmol) and water (150 μL/mmol ester) were added via hypodermic syringe, and the reaction mixture was stirred for 20 h at 100° C. After cooling to r.t. (=21° C.), the solvent was removed in vacuo and ester 3 was obtained after flash column chromatography ($SiO_2$, ethyl acetate-hexane or diethyl ether-hexane).

Ethyl 3-phenylhexanoate (3a). Compound 3a was synthesized following the general procedure from ethyl 5-hexenoate (1a) (75.0 mg, 0.5 mmol) and sodium tetraphenylborate (2a) (343 mg, 1.0 mmol). Purification via flash column chromatography ($SiO_2$, ethyl acetate-hexane 1:8) yielded 3a as a colorless liquid (98 mg, 89%).

CAS-Nr. 99903-38-5 $^1$H NMR (600 MHz, $CDCl_3$) ppm 7.23-7.29 (m, 2H) 7.14-7.18 (m, 3H) 4.00 (q, J=7.1 Hz, 2H) 3.06-3.11 (m, 1H) 2.51-2.62 (m, 2H) 1.54-1.64 (m, 2H) 1.09-1.20 (m, 5H) 0.80-0.88 (m, 3H) ppm. $^{13}$C NMR (101 MHz, $CDCl_3$) 172.3, 144.1, 128.3, 127.4, 126.3, 60.1, 41.9, 41.8, 38.4, 20.4, 14.0, 13.9 ppm. MS (Ion trap, EI): m/z (%)=221 [M⁺] (86), 174 (55), 135 (68), 132 (92), 118 (37), 105 (27), 91 (100).

Preparative scale synthesis of ethyl 3-phenylhexanoate (3a). An oven-dried 50 mL crimp top vial was charged with acetylacetonato(1,5-cyclooctadiene)rhodium(I) (46.5 mg, 0.15 mmol), BIPHEPHOS (124 mg, 0.15 mmol), sodium tetraphenylborate (2a) (6.86 g, 19.9 mmol) and stir bar, sealed with a Teflon septum and evacuated-purged with argon three times. Subsequently, toluene (30 mL), ethyl 5-hexenoate (1a) (1.48 g, 10.0 mmol) and water (1.5 mL) were added via hypodermic syringe, and the reaction mixture was stirred for 20 h at 100° C. After cooling to r.t., the solvent was removed in vacuo and 3a was obtained after flash column chromatography (40 g SiO$_2$, diethyl ether-hexane 1:9) as a colorless liquid (1.75 g, 80%). The results shown that only the use of the selected rhodium catalysts will lead to the wanted β-functionalized products.

TABLE 1

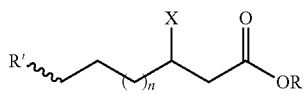

| Entry | Catalyst (mol %) | Ligand (mol %) | XnB—Ph 2 (equiv.) | Yield (%) |
|---|---|---|---|---|
| 1 | [Rh(COD)Cl]$_2$ (0.5) | Biphephos (1.0) | NaBPh$_4$ (1.5) | 40 |
| 2 | [Rh(COD)Cl]$_2$ (0.5) | Biphephos (1.0) | NaBPh$_4$ (2.0) | 47 |
| 3 | — | Biphephos (1.0) | NaBPh$_{4'}$(1.5) | 0 |
| 4 | [Rh(COD)Cl]$_2$ (0.5) | — | NaBPh$_{4'}$(1.5) | 0 |
| 5 | [Rh(OH)Cl)]$_2$ (0.5) | Biphephos (1.0) | NaBPh$_{4'}$(1.5) | 38 |
| 6 | Rh(COD)(acac) (1.0) | Biphephos (1.0) | NaBPh$_{4'}$(1.5) | 57 |
| 7 | Rh(COD)(acac) (1.5) | Biphephos (1.5) | NaBPh$_{4'}$(1.5) | 65 |
| 8 | Rh(COD)(acac) (1.5) | Biphephos (1.5) | NaBPh$_4$ (2.0) | 91 | pin = Pinacol;
MIDA = N-methyliminodiacetic acid boronate;.

The invention claimed is:

1. A method for preparing β-functionalized carboxylic acid esters according to formula (I):

(I)

wherein R is an alkyl group with 1 to 8 C-atoms, R' is a hydrogen atom, or an alkyl group with 1 to 8 C-atoms, n is zero, or a number from 1 to 20, and X is Ph-R", wherein R" represents a hydrogen atom or an alkyl group with 1 to 6 C-atoms, or R'''-N—R'''', wherein R''' and R'''' are each independently linear or branched or cyclic alkyls with 1 to 8 C-atoms, the method comprising reacting in one-pot an unsaturated ester according to general formula (II)

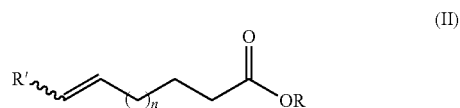

wherein n, R and R' have the same meaning as in formula (I), with either a boron compound according to formula (III) where M represents an anion, and R" has the same meaning as for formula (I),

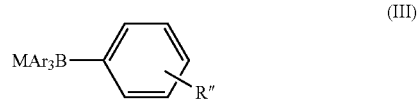

or an amine R'''—NH—R'''' (IV), wherein R''' and R'''' have the same meaning as above and a rhodium containing catalyst, under an oxygen-free atmosphere at temperatures between 80-120° C. in a solvent.

2. The method according to claim 1, wherein R' is hydrogen and R is ethyl on the unsaturated ester according to formula (II).

3. The method according to claim 1, wherein the rhodium containing catalyst comprises a Rh-complex containing a Rh-atom with oxidation number +1.

4. The method according to claim 1, wherein the rhodium containing catalyst comprises (i) Rh(acac)(COD), [Rh(OH)(COD)]$_2$ or [Rh(Cl)(COD)]$_2$ together with (ii) a Biphephos or P(Oallyl)$_3$ ligand in molar amounts of (i): (ii) of 2:1 to 1:2.

5. The method according to claim 1, wherein the solvent comprises benzene, toluene, chlorobenzene, diphenyl ether, or blends of water and the forgoing.

6. The method according to claim 5, wherein the solvent comprises toluene, or a blend of water and toluene in a weight ratio of 1:25 to 1:10.

7. The method according to claim 1, wherein the boron compound according to formula (III) is selected from the group consisting of PhB(OH)$_2$, PhB(pin), PhBMIDA ester, PhBF$_3$K, KB(4-ClC$_6$H$_4$)$_4$, NaB(2-naphthyl)$_4$, NaB(4-tolyl)$_4$, and KB(2-thienyl)$_4$.

8. The method according to claim 6, wherein the solvent comprises a blend of water and toluene in a weight ratio 1:20.

* * * * *